United States Patent [19]

Ekman et al.

[11] Patent Number: 4,732,708
[45] Date of Patent: Mar. 22, 1988

[54] METHOD FOR CONVERTING VEGETABLE MATERIAL INTO CHEMICALS

[75] Inventors: Rainer Ekman; Christer Eckerman, both of Turku; Tapio Mattila; Elias Suokas, both of Espoo, all of Finland

[73] Assignee: Kemira Oy, Helsinki, Finland

[21] Appl. No.: 832,091

[22] Filed: Feb. 20, 1986

[30] Foreign Application Priority Data

Mar. 4, 1985 [FI] Finland .................................. 850863

[51] Int. Cl.$^4$ ........................ C11B 3/08; C07C 51/16; C07C 51/295; C07C 67/39
[52] U.S. Cl. ................................... 260/413; 260/412; 560/190; 562/590; 562/595
[58] Field of Search ................ 260/413, 412; 560/190; 562/590, 595

[56] References Cited

U.S. PATENT DOCUMENTS 2,947,764  8/1960  Zenczak ........................ 260/413 R
3,060,211  10/1962  Mihara et al. ................ 260/413 R Primary Examiner—Werren B. Lone
Assistant Examiner—Vera C. Clarke
Attorney, Agent, or Firm—Pennie & Edmonds

[57] ABSTRACT

The invention relates to a method for converting biopolyesters consisting of straight-chain hydroxyacid monomers containing 10 to 40 carbon atoms, such as suberin and cutin, into a plain mixture of organic acids and their salts containing only a few main components. The depolymerization is carried out according to the invention by oxidizing either with a strong oxidizer or by dehydrating oxidation with strong alkali at elevated temperature.

10 Claims, No Drawings

METHOD FOR CONVERTING VEGETABLE MATERIAL INTO CHEMICALS

This invention relates to a method for converting vegetable material into chemicals and in particular to a method for converting complex biopolyesters of suberin and cutin type consisting of straight-chain hydroxy acid monomers containing 10 to 40 carbon atoms, into a plain mixture of organic acids and their salts, which contains only a few main components.

The purpose of the invention is, particularly, to produce from the side products of the forest industry, such as birch bark, oak cork and the similar suberin and cutin containing raw materials plain chemical mixtures containing as their main components valuable organic acids and their salts, of which the valuable main components can be recovered by separation methods known per se.

For the sake of simplicity, in the first place only birch bark is being dealt with in this context, but the treatment of other plant organs containing suberin and cutin, which have been dealt with e.g. in the publication of Kolattukudy (Science 208 (1980) 990) is analogous to the treatment of birch bark.

According to Kolattukudy suberin and cutin would have the following structural and monomer composition:

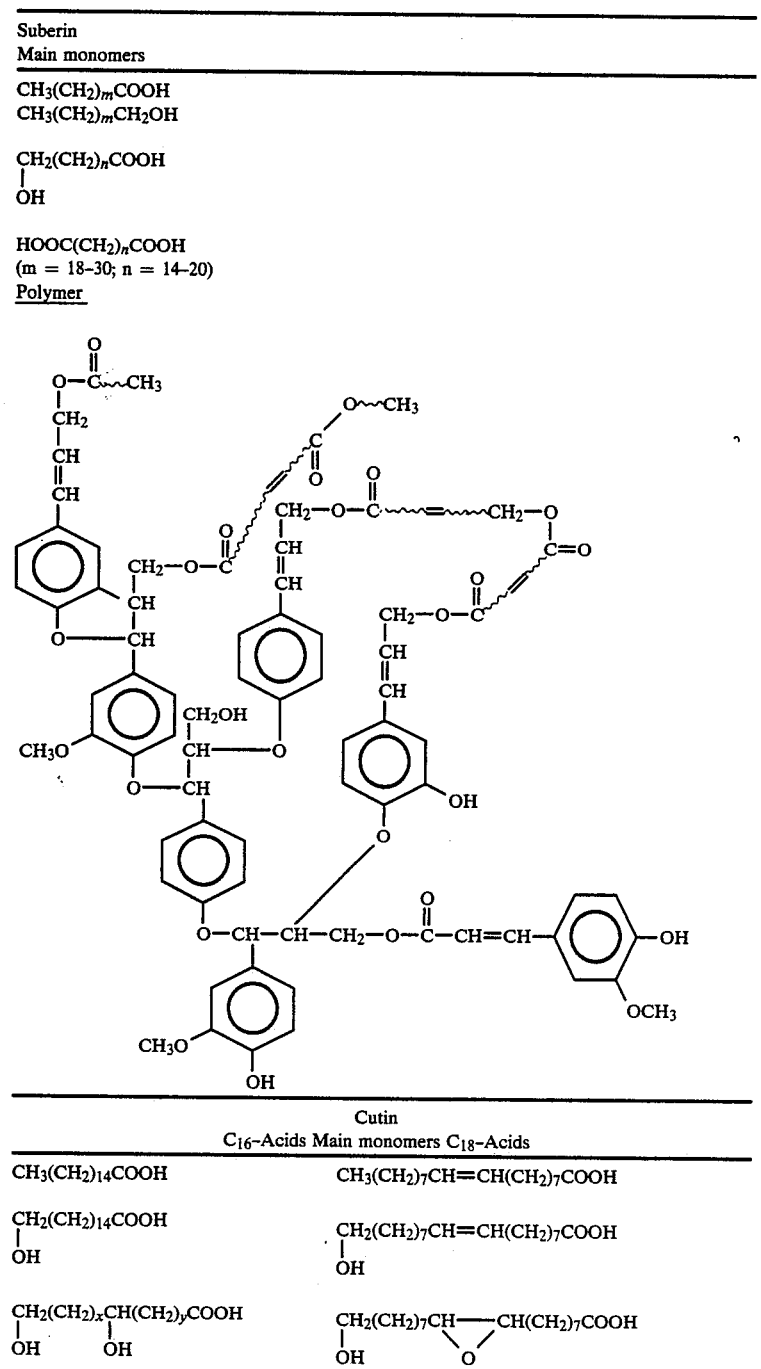

Suberin
Main monomers $CH_3(CH_2)_m COOH$ $CH_3(CH_2)_m CH_2OH$ $\underset{OH}{CH_2(CH_2)_n COOH}$ $HOOC(CH_2)_n COOH$ (m = 18–30; n = 14–20)

Polymer

Cutin
$C_{16}$-Acids Main monomers $C_{18}$-Acids $CH_3(CH_2)_{14}COOH$   $CH_3(CH_2)_7CH=CH(CH_2)_7COOH$ $\underset{OH}{CH_2(CH_2)_{14}COOH}$   $\underset{OH}{CH_2(CH_2)_7CH=CH(CH_2)_7COOH}$ $\underset{OH\quad OH}{CH_2(CH_2)_x CH(CH_2)_y COOH}$   $\underset{OH\quad\ \ O}{CH_2(CH_2)_7CH\!-\!\!-\!\!CH(CH_2)_7COOH}$ -continued (y = 8, 7, 6 tai 5 x + y = 13)

$$CH_2(CH_2)_7CH-CH(CH_2)_7COOH$$
$$\phantom{CH_2(CH_2)_7}|\phantom{CH-}|\phantom{C}|$$
$$\phantom{CH_2(CH_2)_7}OH\phantom{CH}OH\phantom{C}OH$$

Polymer $$\begin{bmatrix}
\text{O} \\
\parallel \\
\text{C—O—CH}_2(\text{CH}_2)_5\text{—CH(CH}_2)_8\text{——C} \overset{\displaystyle\nearrow\text{O}}{\underset{\displaystyle\searrow\text{O}}{}} \\
\quad\quad\quad\quad\quad\quad\quad\quad\quad | \\
(\text{CH}_2)_8 \quad\quad\quad\quad\quad\text{O} \quad\quad\quad\quad\quad \text{CH}_2 \\
|  \quad\quad\quad\quad\quad\quad\quad | \quad\quad\quad\quad\quad\quad |\\
\text{CH—CH} \quad\quad\quad\text{C=O} \quad\quad\quad (\text{CH}_2)_8 \quad\quad\quad\quad\text{O} \\
| \quad\quad\quad\quad\quad\quad\quad | \quad\quad\quad\quad\quad\quad | \quad\quad\quad\quad\quad\parallel\\
(\text{CH}_2)_{15} \quad\quad\quad(\text{CH}_2)_8 \quad\quad\quad\text{CH—O—C—(CH}_2)_{14}\text{CH}_3 \\
| \quad\quad\quad\quad\quad\quad\quad | \quad\quad\quad\quad\quad\quad | \\
\text{CH}_2 \quad\quad\quad\text{CH—OH} \quad\quad\quad(\text{CH}_2)_8 \\
| \quad\quad\quad\quad\quad\quad\quad | \quad\quad\quad\quad\quad\quad | \\
\text{O} \quad\quad\quad\quad(\text{CH}_2)_8 \quad\quad\quad\text{C=O} \\
\phantom{|}\searrow\quad\quad\quad\quad | \quad\quad\quad\quad\quad\quad | \\
\quad\quad\quad\text{CH}_2\text{—O—C—(CH}_2)_{14}\text{CH}_2\text{—O} \\
\quad\quad\quad\quad\quad\quad\parallel \\
\quad\quad\quad\quad\quad\quad\text{O} \\
\\
\searrow\text{C—(CH}_2)_8\text{—CH—(CH}_2)_5\text{CH}_2\text{O—C—(CH}_2)_8\text{CH(CH}_2)_5\text{CH}_2\text{—O} \\
\parallel \quad\quad\quad\quad\quad | \quad\quad\quad\quad\quad\quad\parallel \quad\quad\quad\quad\quad\quad | \\
\text{O} \quad\quad\quad\quad\quad\text{O} \quad\quad\quad\quad\quad\quad\text{O} \quad\quad\quad\quad\quad\quad\text{O} \\
\quad\quad\quad\quad\quad\quad | \\
\quad\quad\quad\quad\quad\quad\text{C=O} \\
\quad\quad\quad\quad\quad\quad | \\
\quad\quad\quad\quad\quad\quad\text{CH} \\
\quad\quad\quad\quad\quad\quad\parallel \\
\quad\quad\quad\quad\quad\quad\text{CH} \\
\quad\quad\quad\quad\quad\quad | \\
\quad\quad\quad\quad\quad\quad\text{C}_6\text{H}_4\text{—OH}
\end{bmatrix}$$

The previous methods for the decomposition and separation of suberin into components comprise, for example, the alkaline hydrolysis, the alkaline or acid catalyzed exchange esterification or the reduction with aluminum lithium hydride (Holloway, P. J. in Plant Cuticle, Eds. D. F. Cutter, K. L. Ahein and C. E. Price, Linnean Society Symposium Series No. 10, Academic Press, London 1982).

By these methods it is possible to produce monomeric hydroxy and carboxylic acids from birch bark by separating them from the other main components of birch bark, i.e. betulin and the non-aliphatic part. The mixture of the organic acids obtained is, however, very pennached and it is difficult to separate it into components, which fact in general, is one of the greatest drawbacks of chemicals originating from nature in view of their economical utility. A good example of this are the attempts to utilize lignin by decomposing it to plain components.

Now it has unexpectedly been found that the suberin of birch bark can, as a new industrial raw material, be decomposed to a substantially simpler mixture of a few components, which can easily be separated to usable fractions.

According to the invention the suberin and cutin type biopolyester raw material mixture is converted by depolymerization with acid or alkali and by oxidation either with a strong oxidant or dehydration strong alkali at a high temperature either directly or then the raw material is first exposed to acidic or alkaline hydrolysis is a polar organic solution and/or water, whereafter the oxidation is carried out on the monomer mixture thus separated from the solids.

The dehydration oxidation can be carried out with sodium or potassium hydroxide or with their mixture at so high a temperature that the alkali is in molten state, preferably at 200° to 400° C., for example at 280° to 350° C., or in a strong alkali solution, whereby the raising of the temperature to a sufficient level may involve the use of excess pressure to prevent the evaporation of the water.

When suberin is first treated with alkali or acid in water, lower alcohol or their mixture, a complicated mixture of hydroxy and dicarboxylic acids or the esters of their lower alcohol is obtained and then, further, a simple mixture of carboxylic acids by oxidation in accordance with the invention with strong oxidants, such as potassium permanganate, nitric acid, ruthenium tetroxide, ozone, chromic acid, etc., or with dehydration oxidation in strong alkali at a high temperature. The mixture obtained by the method in accordance with the invention is, as will be shown later on, simple as to its composition and useful for the preparation of some mono- and dicarboxylic acids. In the following the method in accordance with the invention is described in further detail.

Great amounts of birch bark is formed in the various industrial fields in which birch is used as raw material of different kinds of refinement processes. Such industrial fields are the pulp, sawmill, chipboard, plywood and furniture industry, in which great amounts of birch bark is often gathered in the dumping areas. oak bark is formed respectively in industry using oak and as residue in the refinement of the cork oak's cork.

The main components of the outer layer of the bark of birch, the birch bark, are biopolyester (suberin), triterpene alcohols as well as a mixture comprising principally polymeric compounds containing among others phenolic components. Suberin and triterpene alcohols form together about 60% by weight of the birch bark. The triterpene alcohols can be removed from the birch bark by extracting with an organic solvent. As suberin is virtually insoluble in organic solvents, it can be concentrated into a solid extract residue. The amount of suberin thus increases to about 50% by weight of the extracted birch bark. It has been contended above that suberin is a polyester consisting of polymerized, straight-chain, even $C_{16}$ to $C_{24}\omega$-hydroxy fatty acids, some of which furthermore includes epoxy or hydroxyl groups in the middle of the carbon chain as well as of $\omega$-dicarboxylic acids. The polar monomer component is the 9,10-epoxy-18-hydroxyoctadecane acid, which comprises about 30–43% of the monomer composition.

Suberin can be hydrolyzed to its monomeric components both with acids and with alkalis in an aqueous solution and in polar organic solvents. The selectivity of the hydrolysis can be adjusted by controlling the concentration of the acid or the alkali, the reaction circumstances and the solvent, in order to achieve the final result desired in each case.

An exhaustive hydrolysis of suberin with 0.5M alkali hydroxide in a 95% solution of a lower alcohol gives about 500 g monomers from one kilogram extracted birch bark. The composition of the monomer mixture obtained is disclosed in Table 1. As can be seen from the table, the 9,10-epoxy-18-hydroxyoctadecane acid and the 22-hydroxydocosane acid are the main components of the mixture.

A corresponding result is obtained by an acid hydrolysis in a solution of a lower alcohol with the difference that the products are in the form of lower alcohol esters and the 9,10-epoxy group has reacted forming 9(10)-methoxy-10(9)-hydroxy- and 9,10-dihydroxy derivatives as well as reproduction products of the epoxy group. The hydrolyses described above can be carried out also for unextracted birch bark with similar results.

The monomer mixture obtained by the above-described hydrolysis methods on extracted or unextracted birch bark can be treated further so that the terminal hydroxy groups comprised therein are converted into carboxylic acid groups and into dicarboxylic acid groups and the above-mentioned functional groups in the carbon chain are oxidized and the carbon chain broken forming dicarboxylic acids. The treatment methods that come into question can be selected from oxidations by various strong oxidizers, such as potassium permanganate, nitric acid, ruthenium tetroxide, ozone, or chromic acid or by dehydration in strong alkali at a high temperature (alkali melting). Chemically, oxidation of alcohols to carboxylic acids occur in these treatments.

The above-mentioned methods produce from a complex mixture of suberin monomers, depending on the method used, either only straight-chain saturated dicarboxylic acids (Table 4) or, if alkali is used as the oxidant, due to the mechanism, also short-chain monoacids (Table 3). As can be seen from Tables 3 and 4, the mixture has been considerably similified and concentrated in regard to certain acids and the mixture has been brought to such a state that further refining can be carried out by conventional means.

The acid mixture obtained by the method in accordance with the invention can be divided into its components by conventional methods, e.g. by crystallization from organic solvents or by liquid-liquid extraction. The short-chain fatty acids can also be distilled from mixtures of dicarboxylic acids at subatmospheric pressure and thereafter the dicarboxylic acids can be separated e.g. according to the chain length by fractional crystalliztion or by subatmospheric pressure distillation into two fractions, nonanediacid (azelaic acid) and the mixture of hexadecanedocosanediacid, which already as such are technically useful in the preparation of various derivatives.

A more detailed but non-limiting description of the invention is provided below by way of the following examples.

EXAMPLE 1

(Prior Art)

10 g of extracted, milled birch bark was charged to 500 ml column, which was equipped with a reflux cooler and a magnetic mixer. 250 ml of 0.5M sodium hydroxide solution of 90% ethanol was added to the column and the mixture was refluxed for 1 hour. After this the precipitate was filtered off and washed with hot ethanol and the monomers were analyzed from the solution after the acidification and diethyl ether extraction as silyl ether derivatives of their methyl esters with gas chromatography. The monomer yield was over 90% calculated from the suberin of the dry birch bark. The composition of the product obtained is disclosed in Table 1 and its treatment was continued in accordance with Example 4.

EXAMPLE 2

(Prior Art)

The hydrolysis was repeated as in the preceding example with the exception that water was used instead of ethanol and the reaction time was 3 hours. The monomer yield was over 95% calculated from the suberin of the dry birch bark. The suberin monomer composition of the hydrolysate obtained is disclosed in Table 1.

EXAMPLE 3

2 g of extracted birch bark was charged to 250 ml flask, which was equipped with a reflux cooler and a magnetic stirrer. 90 ml of methanol and 10 ml of 96% $H_2SO_4$ were added to the flask and the mixture was refluxed for 3 hours. The methyl esters of the monomers of suberin were analyzed after silylation with a gas chromatograph. The yield of the methyl esters of monomers was about 90%. The composition of the product obtained is disclosed in Table 2.

EXAMPLE 4

To the dried salt mixture of monomers (0.5 g) obtained in the preceding example 1 was added 3 g of potassium hydroxide dissolved in 2 ml of water. The mixture was heated under agitation in a nickel crucible in a tin bath at a temperature of 330° C. for 15 minutes. The carboxylic acids obtained were analyzed as methyl esters with a gas chromatograph. The yield of the reaction calculated from the free monomers was 90%. The composition of the product obtained is disclosed in Table 3. If the batch is greater it is possible to operate with remarkably smaller, nearly equivalent amounts of alkali.

EXAMPLE 5

To the finely milled cork powder (0.5 g) was added 3 g of potassium hydroxide dissolved in 2 ml of water.

The mixture was heated in a nickel crucible in a tin bath at a temperature of 330° C. for 15 minutes. The carboxylic acids obtained were analyzed after methylation gas chromatographically. The yield of the reaction calculated from the cork suberin was about 90%. The composition of the carboxylic acid obtained is disclosed in Table 3. When the batch is greater it is possible to operate with remarkably smaller, nearly equivalent amounts of alkali.

EXAMPLE 6

To the salt mixture (0.5 g) of the suberin monomer obtained in Example 1 was added 3 ml of 1N sodium hydroxide solution and the solution was refluxed for 16 hours. After this 15 ml of a 0.5M aqueous solution of potassium permanganate was added to the mixture which was heated at 50° C. in 0.5 hours. The solution was acidified with 3N sulphuric acid and extracted 5 times with diethyl ether and analyzed as in Example 5. The composition of the carboxylic acid mixture obtained is disclosed in Table 4.

EXAMPLE 7

3 ml of water was added to the dried salts of the suberin monomer mixture (9.2 g) obtained in Example 1 and the pH of the mixture was adjusted to 3.5 with 50% H SO. The suberin acids released were extracted with diethyl ether and the ether solution was evaporated to a dryness. The evaporation residue was dissolved in 5 ml acetone Jones-reagent was added dropwise until the colour of the oxidant remained. The Jones-reagent was prepared by dissolving 26.72 g of chromium trioxide in 100 ml of sulfuric acid, which was obtained by diluting 23 ml of concentrated $H_2SO_4$ with water to 100 ml.

During the oxidation the reaction was monitored with a gas chromatograph as presented above. The compositions of the products obtained with strong oxidants are disclosed in Table 4.

TABLES

TABLE 1

The composition of products obtained in alkali hydrolysis of birch bark suberin

| Carboxylic acid | Example | |
|---|---|---|
| | 1 | 2 |
| Octadec-9-ene diacid | 4.7 | 4.2 |
| 18-hydroxyoctadec-9-ene acid | 12.2 | 11.7 |
| 9,10-epoxy-18-hydroxyoctadecanoic acid | 39.2 | 19.8 |
| 9,10,18-trihydroxyoctadecanoic acid | 8.4 | 28.8 |
| Docosane diacid | 8.2 | 8.1 |
| 22-hydroxydocasanoic acid | 13.9 | 13.3 |
| Others ($C_{16}$–$C_{24}$) | 13.4 | 14.1 |
| | 100.0 | 100.0 |

TABLE 2

The composition of the product obtained with acid methanolysis of birch bark suberin

| Carboxylic acid ester | Percentage of mixture |
|---|---|
| Methyloctadec-9-enedioate | 4.6 |
| Methyl-18-hydroxyoctadec-9-enoate | 11.2 |
| Methyl-9(10)-methoxy-10(9),18-dihydroxy-octadecanoate | 29.8 |
| Methyl-9,10,18-trihydroxyoctadecanoate | 13.8 |
| Methyldocosanedioate | 8.0 |
| Methyl-22-hydroxydocosanoate | 11.9 |
| Others $C_{16}$–$C_{24}$ methyl esters | 20.7 |

TABLE 2-continued

The composition of the product obtained with acid methanolysis of birch bark suberin

| Carboxylic acid ester | Percentage of mixture |
|---|---|
| | 100.0 |

TABLE 3

The compositions of products obtained with alkali melting of birch bark suberin monomers and cork suberin

| Carboxylic acid | Example | |
|---|---|---|
| | 4 | 5 |
| octanoic acid | 13.5 | 5.5 |
| Nonane diacid | 24.4 | 16.9 |
| Decane diacid | 2.3 | 2.0 |
| Hexadecane diacid | 15.0 | 17.0 |
| Octadecane diacid | 3.2 | 2.1 |
| Eicosane diacid | 3.6 | 2.6 |
| Docosane diacid | 20.8 | 24.1 |
| Others | 17.2 | 29.8 |
| | 100.0 | 100.0 |

TABLE 4

The composition of products obtained with strong-oxidants from birch bark suberin

| Carboxylic acid | Percentage of mixture | |
|---|---|---|
| Oxidant | $KMnO_4$ | Chromic acid |
| Heptane diacid | 9.3 | 1.0 |
| Octane diacid | 46.2 | 12.9 |
| Nonane diacid | 15.7 | 48.5 |
| Others[1] | 24.9 | 37.6 |
| | 100.0 | 100.0 |

[1]Comprises eicosane diacid and docosane diacid as main components

We claim:

1. Method for converting suberin and cutin type biopolyesters comprising straight chain hydroxyacid monomers containing 10 to 40 carbon atoms into a plain mixture of organic acids and their salts containing only a few main components, characterized in that the conversion is carried out by depolymerization with acid or alkali and by oxidation with a strong oxidant or strong alkali at elevated temperature.

2. Method according to claim 1, characterized in that the oxidation step is carried out at 200°–400° C.

3. Method according to claim 1, characterized in that the oxidation is carried out with an aqueous solution of potassium permanganate or chromic acid.

4. Method according to claim 2, characterized in that the oxidation is carried out at 280°–350° C.

5. Method according to claim 4, characterized in that the oxidation is carried out at about 330° C.

6. Method according to claim 2, characterized in that the oxidation is carried out with sodium hydroxide and/or potassium hydroxide at said elevated temperature.

7. Method according to claim 3, characterized in that the oxidation is carried out at about 50° C.

8. Method according to any one of claims 1–3, 4–7, characterized in that finely divided birch bark and/or oak cork is used as the biopolyester source.

9. Method according to any one of claims 1–3, 4–7, characterized in that birch bark and/or oak cork extracted with an organic solvent is used as the biopolyester source.

10. Method according to any one of claims 1–3, 4–7, characterized in that the depolymerization step comprises the hydrolysis of the biopolyester material in an acidic or alkaline, polar organic solvent and/or water followed by the separation of the monomers obtained thereby from the rest of the solids.

* * * * *